(12) United States Patent　　(10) Patent No.: US 12,582,740 B2
Wada et al.　　(45) Date of Patent: Mar. 24, 2026

(54) INFECTION PREVENTION DEVICE AND INFECTION PREVENTION METHOD

(71) Applicant: RIKEN, Wako (JP)

(72) Inventors: Satoshi Wada, Saitama (JP); Atsushi Shinjo, Saitama (JP); Takayo Ogawa, Saitama (JP)

(73) Assignee: RIKEN, Wako (JP)

( * ) Notice: Subject to any disclaimer, the term of this patent is extended or adjusted under 35 U.S.C. 154(b) by 481 days.

(21) Appl. No.: 18/017,837

(22) PCT Filed: Jun. 22, 2021

(86) PCT No.: PCT/JP2021/023512

§ 371 (c)(1),
(2) Date: Jan. 24, 2023

(87) PCT Pub. No.: WO2022/024589

PCT Pub. Date: Feb. 3, 2022

(65) Prior Publication Data

US 2023/0256130 A1　Aug. 17, 2023

(30) Foreign Application Priority Data

Jul. 27, 2020　(JP) ................................. 2020-126458
Sep. 28, 2020　(JP) ................................. 2020-162242

(51) Int. Cl.
　A61N 5/00　　　(2006.01)
　A61L 2/00　　　(2006.01)
　　　(Continued)

(52) U.S. Cl.
　CPC ..................................... A61L 9/20 (2013.01);
　　　A61L 2/08 (2013.01); A61L 2/10 (2013.01);
　　　　　　　　　　　　　A61L 2/26 (2013.01);
　　　(Continued)

(58) Field of Classification Search
　CPC ..... A61L 2/08; A61L 2/10; A61L 9/20; A61L 2202/25; A61L 2209/212; F21V 29/83
　　　(Continued)

(56) References Cited

U.S. PATENT DOCUMENTS

2015/0247615 A1* 9/2015 Matsui .................... F21V 29/83
　　　　　　　　　　　　　　　　　250/492.1

FOREIGN PATENT DOCUMENTS

CN　　111265706 A　　6/2020
JP　　2006-231007 A　　9/2006
　　　(Continued)

OTHER PUBLICATIONS

International Search Report for International Application No. PCT/JP2021/023512 dated Aug. 3, 2021 (3 sheets).

(Continued)

*Primary Examiner* — Monzer R Chorbaji
(74) *Attorney, Agent, or Firm* — Kratz, Quintos & Hanson, LLP

(57)　　　ABSTRACT

The present invention provides an infection prevention device and an infection prevention method including a light source 11 for radiating light in specific wavelength range, and a beam-firming optical element 12 for forming the light radiated from the light source 11 on a radiant film 20 having a predetermined width, wherein pathogenic microorganism which levitates together with airborne droplets or particles or which levitates alone is inactivated or killed by the radiant film 20 formed in air, or moisture of the airborne droplets or the particles is evaporated. According to this, pathogenic microorganism which levitates in air can be inactivated or killed in air.

24 Claims, 8 Drawing Sheets

(51) Int. Cl.

| | |
|---|---|
| *A61L 2/08* | (2006.01) |
| *A61L 2/10* | (2006.01) |
| *A61L 2/26* | (2006.01) |
| *A61L 9/18* | (2006.01) |
| *A61L 9/20* | (2006.01) |

(52) U.S. Cl.
CPC .............. *A61L 9/18* (2013.01); *A61L 2202/11* (2013.01); *A61L 2202/14* (2013.01); *A61L 2202/25* (2013.01); *A61L 2209/111* (2013.01); *A61L 2209/12* (2013.01)

(58) Field of Classification Search
USPC .......................................... 422/24; 250/492.1
See application file for complete search history.

(56) References Cited

FOREIGN PATENT DOCUMENTS

| | | | |
|---|---|---|---|
| JP | 2007-533350 | A | 11/2007 |
| JP | 2011-098156 | A | 5/2011 |
| JP | 2011-137588 | A | 7/2011 |
| JP | 2013-019894 | A | 1/2013 |
| JP | 2014-089898 | A | 5/2014 |
| JP | 2018-007804 | A | 1/2018 |
| KR | 20180078832 | A | 7/2018 |
| WO | 2021/249668 | A1 | 12/2021 |

OTHER PUBLICATIONS

Supplementary Partial European Search Report for European Application No. 21848567.0 dated Jul. 30, 2024 (6 sheets).
Communication pursuant to Article 94(3) EPC in corresponding European Patent Application No. 21848567.0 dated Jan. 20, 2026 (11 sheets).

* cited by examiner

[Figs. 1]
(a)
11(10)
12(10)
20
13(10)
(b)
11
12
X X
20
13
(c)
X 20
11
12
13
X
(d)
Width
Thickness
20
(e)
Width
Thickness
20
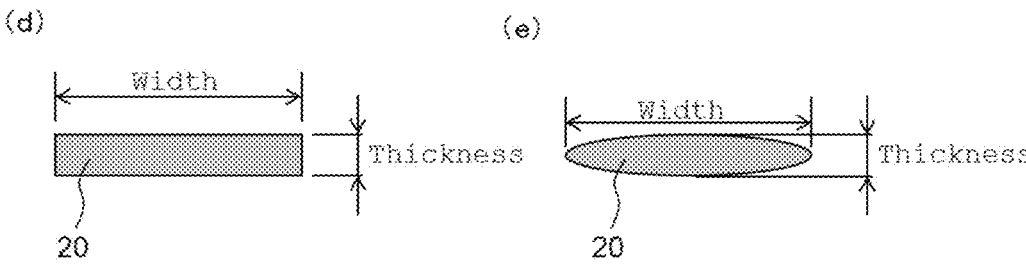

[Figs. 2]
(a)
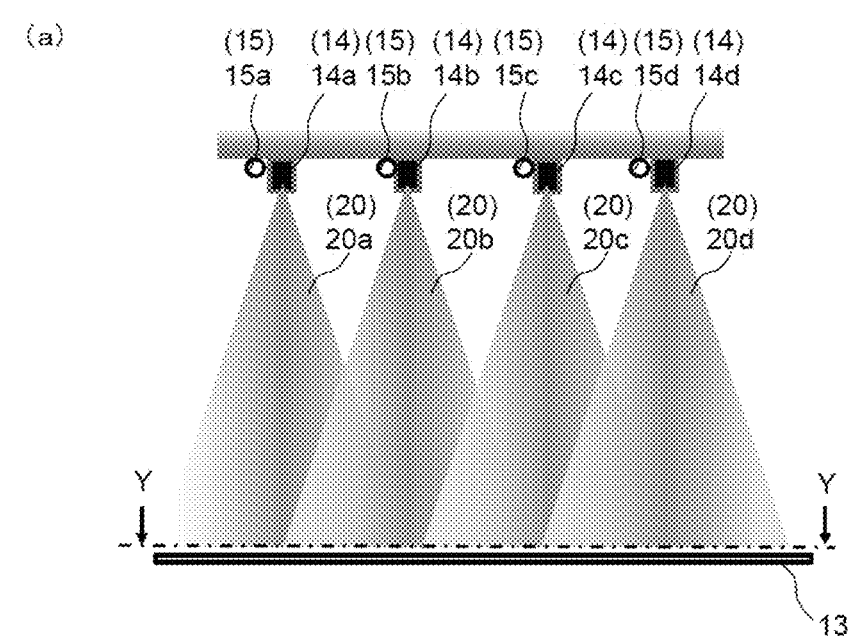
(b)
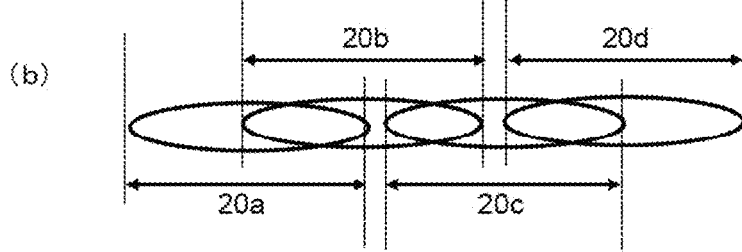
(c)
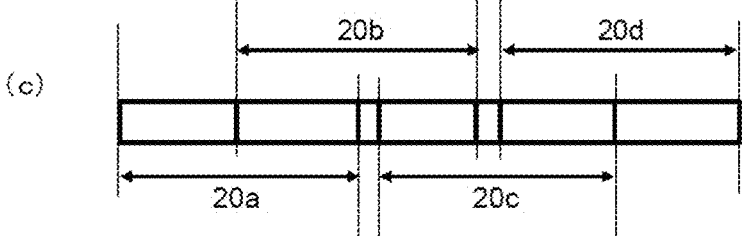

[Figs. 3]
(a)
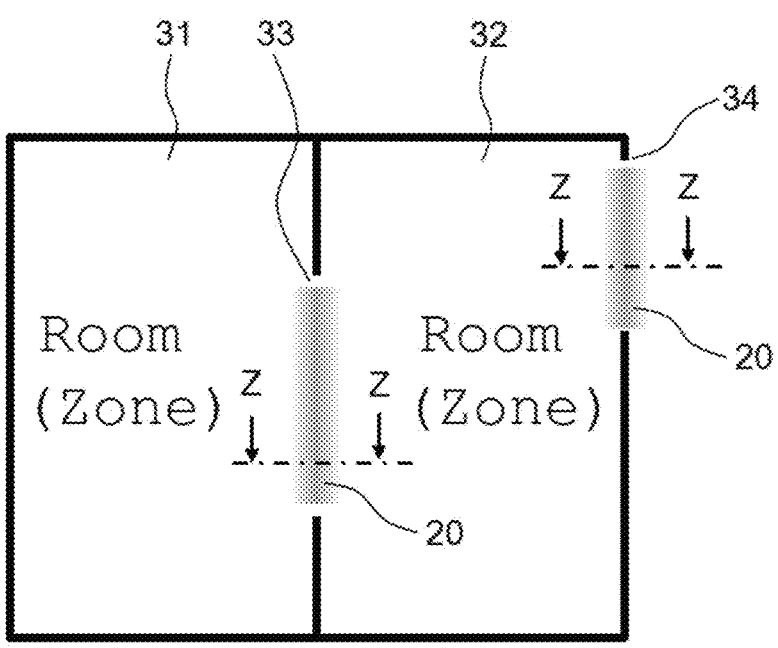
(b)          (c)
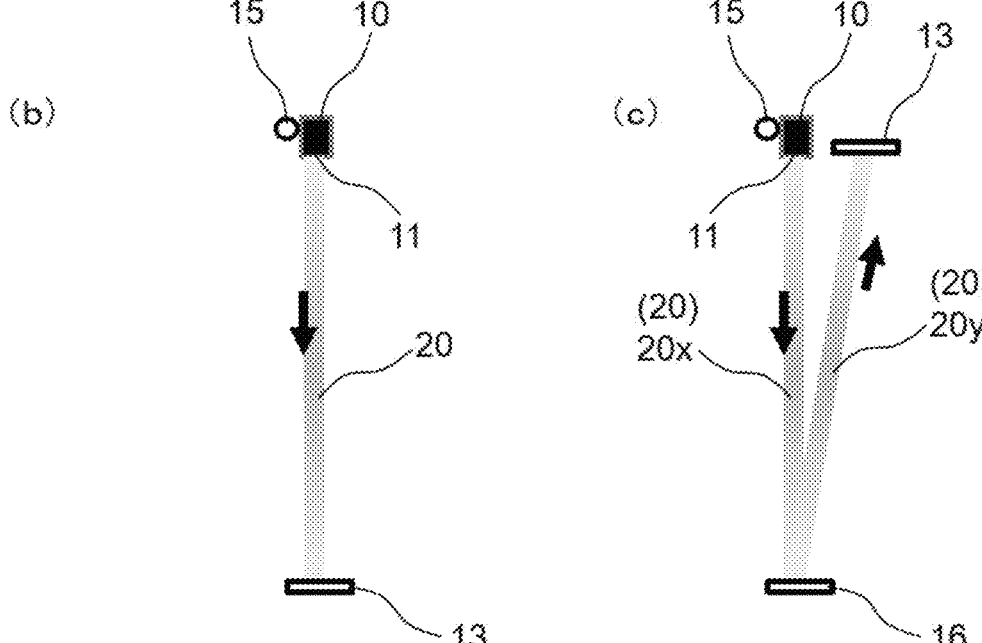

[Fig. 4]
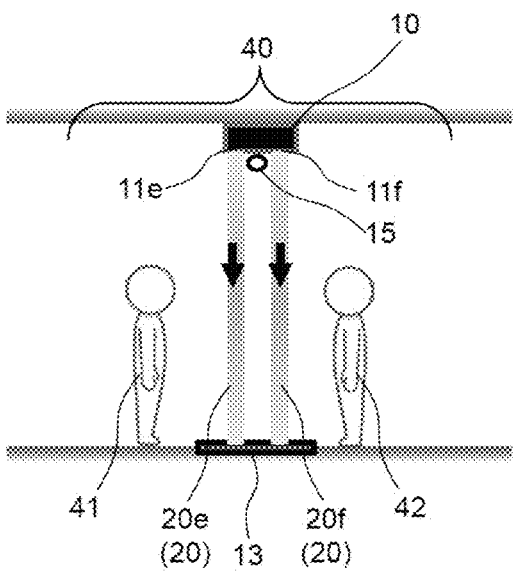

[Fig. 5]
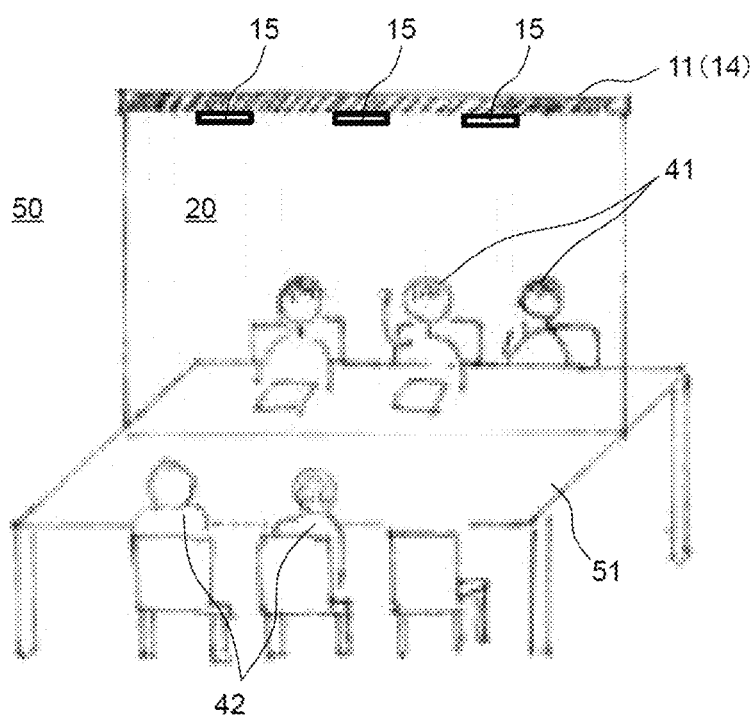

[Fig. 6]
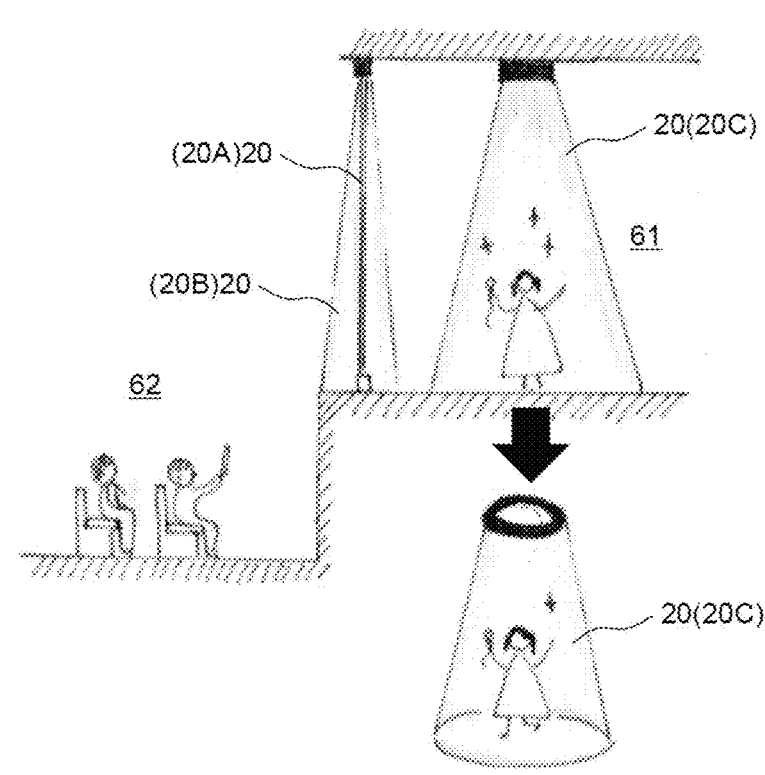

[Fig. 7]
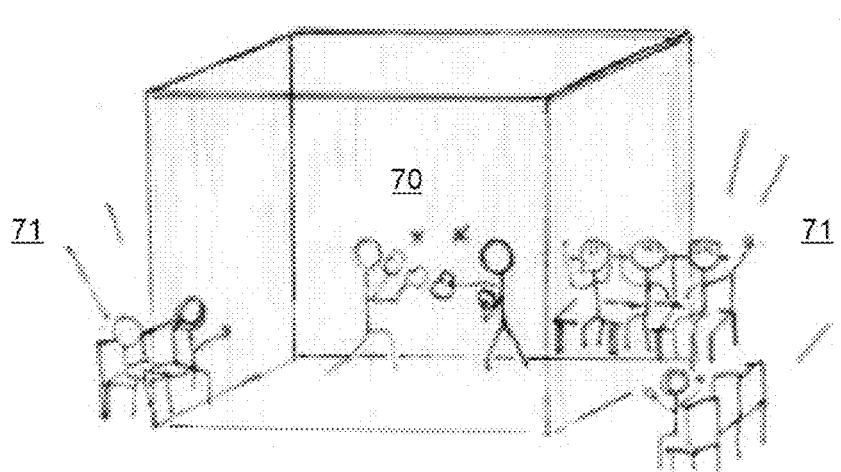

[Figs. 8]
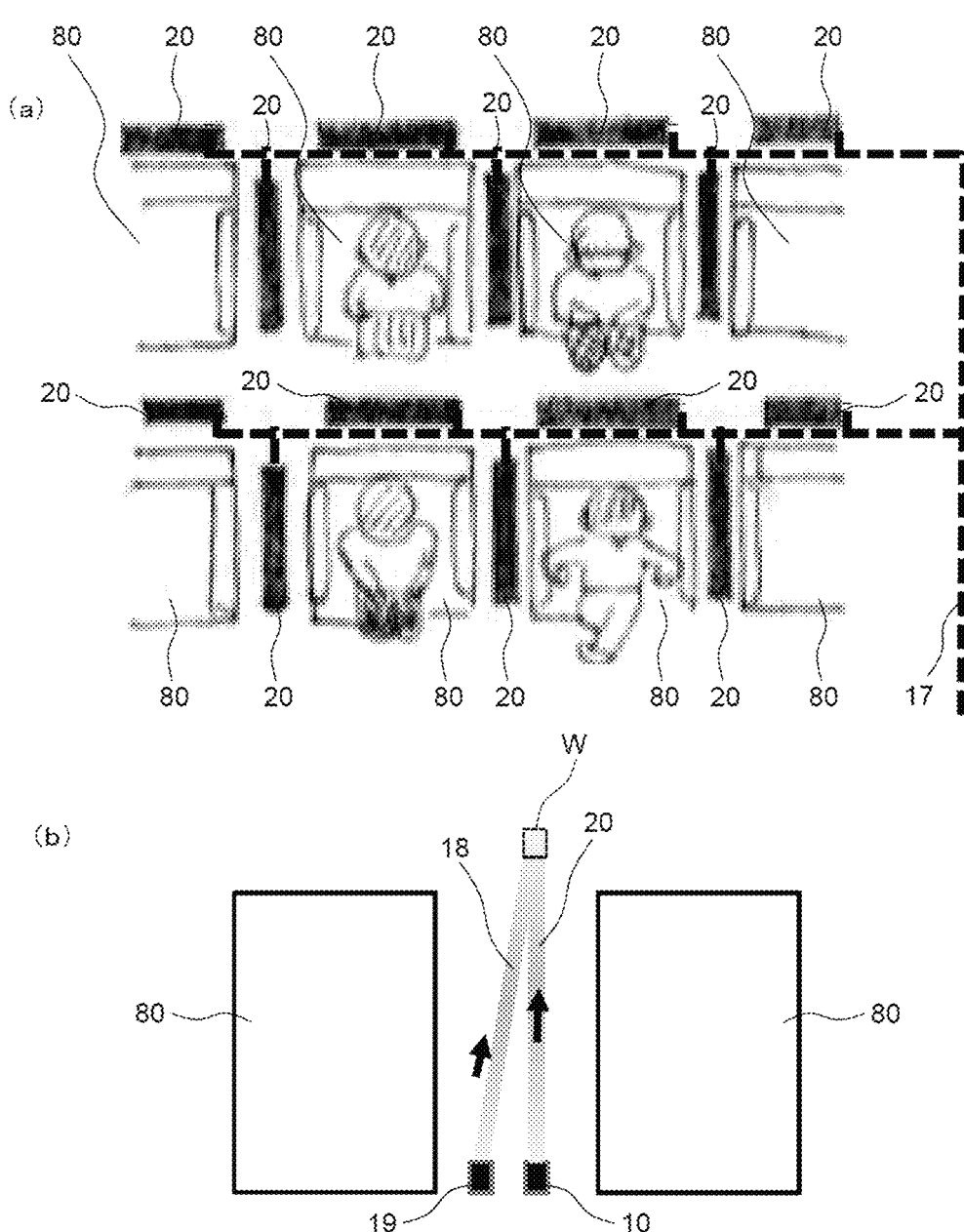

INFECTION PREVENTION DEVICE AND INFECTION PREVENTION METHOD

TECHNICAL FIELD

The present invention relates to an infection prevention device and an infection prevention method for inactivating or killing pathogenic microorganism which levitates together with airborne droplets or particles or which levitates along.

BACKGROUND TECHNIQUE

Presently, COVID-19 becomes a social problem, and has a large civilizing influence.

It is conventionally known that ultraviolet shine is effective to inactivate virus.

Patent documents 1 to 7 propose a method to inactivate virus using ultraviolet shine.

Patent documents 8 and 9 propose an ultraviolet light sterilizing device having a sterilization light beam film generating section for generating a film-like sterilization light beam film.

PRIOR ART DOCUMENTS

Patent Documents

[Patent Document 1] Japanese Patent Application Laid-open No. H11-286453
[Patent Document 2] Japanese Patent Application Laid-open No. 2012-143249
[Patent Document 3] Japanese Patent Application Laid-open No. 2015-171440
[Patent Document 4] Japanese Patent Application Laid-open No. 2006-519003
[Patent Document 5] Japanese Patent Application Laid-open No. 2013-534816
[Patent Document 6] Japanese Patent Application Laid-open No. 2014-533942
[Patent Document 7] Japanese Patent Application Laid-open No. 2013-78650
[Patent Document 8] Japanese Patent No. 6188969
[Patent Document 9] Japanese Patent No. 6587783

SUMMARY OF THE INVENTION

Object to Be Solved By the Invention

However, according to the patent documents 1 to 7, to sufficiently inactivate virus by ultraviolet shine, solution or filter is irradiated, solution is irradiated with ultraviolet shine, or virus collected by the filter is irradiated with ultraviolet shine, and pathogenic microorganism which levitates is not inactivated or killed in air.

In the patent documents 8 and 9, sterilization light beam film is generated in a cylindrical casing, or the sterilization light beam film is not formed by ultraviolet rays radiated from an ultraviolet ray source, and the sterilization light beam film is formed by reflecting at a plurality of reflection sections.

That is, when sterilization photofilm is formed by utilizing reflection as proposed in the patent documents 8 and 9, if an obstacle exists in a portion of the sterilization photofilm, the sterilization photofilm cannot be formed and unexpected reflection light is generated. Therefore, this proposal is not suitable in a space where people exist.

It is an object of the present invention to provide an infection prevention device and an infection prevention method capable of inactivating or killing, in air, pathogenic microorganism which levitates in air.

Mean for Solving Problem

An infection prevention device 10 of the present invention described in claim 1 includes a light source 11 for radiating light in specific wavelength range, and a beam-firming optical element 12 for forming the light radiated from the light source 11 on a radiant film 20 having a predetermined width, wherein pathogenic microorganism which levitates together with airborne droplets or particles or which levitates alone is inactivated or killed by the radiant film 20 formed in air, or moisture of the airborne droplets or the particles is evaporated.

According to the invention described in claim 2, the infection prevention device 10 described in claim 1, further including a damper 13 placed on a terminal end of the radiant film 20, wherein the damper 13 is made of low reflection material.

According to the invention described in claim 3, in the infection prevention device 10 described in claim 1 or 2, the radiant film 20 is formed in a doorway 33, 34 of a room or a zone 31, 32.

According to the invention described in claim 4, in the infection prevention device 10 described in claim 1 or 2, the radiant film 20 is formed between opposed persons 41, 42.

According to the invention described in claim 5, in the infection prevention device 10 described in claim 1 or 2, the radiant film 20 is formed between a stage 61 and an audience seat 62.

According to the invention described in claim 6, in the infection prevention device 10 described in claim 1 or 2, the radiant film 20 is formed into a cylindrical shape, and a space is formed in the radiant film 20 which is formed into the cylindrical shape.

According to the invention described in claim 7, in the infection prevention device 10 described in claim 1 or 2, the radiant film 20 is formed on an outer periphery of a game space 70.

According to the invention described in claim 8, in the infection prevention device 10 described in claim 1 or 2, further comprising g at least one more radiant film 20, wherein the radiant film 20 or the radiant films 20 are formed on a side or in front of or behind a seat 80.

According to the invention described in claim 9, in the infection prevention device 10 described in any one of claims 1 to 8, the light source 11 and the beam-firming optical element 12 are placed at high positions, and the radiant film 20 is formed by radiating the light from upward to downward.

According to the invention described in claim 10, in the infection prevention device 10 described in any one of claims 1 to 9, the light source 11 is composed of a coherent light source, an ultraviolet ray laser or laser, and a wavelength converting device.

According to the invention described in claim 11, in the infection prevention device 10 described in any one of claims 1 to 10, as the beam-firming optical element 12, at least any one of a beam expander which widens the light, a cylindrical lens which makes the light laterally long, and a condenser lens which makes the light as parallel light is used.

According to the invention described in claim 12, in the infection prevention device 10 described in claim 2, as the damper 13, black almite is used.

In an infection prevention device 10 described in claim 13, a lamp, a light-emitting diode or a semiconductor laser is used as a light source 14 which radiates light in specific wavelength range, and pathogenic microorganism which levitates together with airborne droplets or particles or which levitates along is inactivated or killed by forming, in air, a radiant film 20 having a predetermined width by the light radiated from the light source 14.

According to the invention described in claim 14, in the infection prevention device 10 described in any one of claims 1 to 13, the specific wavelength range is wavelength range in a range of 190 nm to 350 nm, and the radiant film 20 is formed by average output of 20 W or less per 1 m width.

According to the invention described in claim 15, in the infection prevention device 10 described in any one of claims 1 to 13, the specific wavelength range is infrared radiation range of 800 nm or more.

According to the invention described in claim 16, in the infection prevention device 10 described in any one of claims 1 to 9, an ultrashort pulse laser is used as the light source 11, and the specific wavelength range is a visual radiation region or an infrared radiation range of 400 nm or more.

According to the invention described in claim 17, in the infection prevention device 10 described in any one of claims 1 to 16, the radiant film 20 is turned back around a reflection plate 16, thereby forming at least two radiant films 20 (20x, 20y), According to the invention described in claim 18, in the infection prevention device 10 described in claim 17, the first radiant film 20x (20) and the second radiant film 20y (29) are not parallel to each other.

According to the invention described in claim 19, in the infection prevention device 10 described in any one of claims 1 to 16, further comprising at least one more light source, thereby forming at least two radiant films 20 (20e, 20f).

According to the invention described in claim 20, in the infection prevention device 10 described in claim 19, center wavelengths of the light sources 11e and 11f are different from each other.

According to the invention described in claim 21, in the infection prevention device 10 described in any one of claims 1 to 20, further including a detector 15 which detects scattering light from the radiant film 20, and if the detector 15 detects the scattering light of a predetermined value or more, radiation of the light from the light source 11 is stopped.

According to the invention described in claim 22, in the infection prevention device 10 described in claim 21, the detector 15 is placed on the side of the light source 11, and a detection direction of the detector 15 is a radiation direction of the light.

According to the invention described in claim 23, in the infection prevention device 10 described in claim 1 or 13, interference light 18 in a wavelength range which is different from the specific wavelength range of the light which forms the radiant film 20 is radiated to the radiant film 20, and a position where the interference light 18 is radiated is at a terminal end of the radiant film 20.

An infection prevention method of the invention described in claim 24, a radiant film 20 having a predetermined width is formed by light in a specific wavelength range, pathogenic microorganism which levitates together with airborne droplets or particles or which levitates alone is inactivated or killed, or moisture of the airborne droplets or the particles is evaporated.

Effect of the Invention

According to the present invention, levitating pathogenic microorganism is inactivated or killed, or airborne droplets or particles are evaporated, thereby effectively preventing infection especially in an overcrowding, cohesive and closed room.

BRIEF DESCRIPTION OF THE DRAWINGS

FIG. 1 are diagrams showing a configuration of an infection prevention device according to an embodiment of the present invention;

FIG. 2 are diagrams showing a configuration of an infection prevention device according to another embodiment of the invention;

FIG. 3 are a plan view and side views of essential portions of rooms or zones where a forming position of a radiant film formed by the infection prevention device shown in FIG. 1 or 2 is partitioned by a predetermined partition;

FIG. 4 is a side view of a predetermined space where the forming position of the radiant film is a room or the like;

FIG. 5 is a perspective view of a predetermined space where the forming position of the radiant film is a conference room;

FIG. 6 is a side view showing a portion of a hall in which the forming position of the radiant film includes a stage and audience seats;

FIG. 7 is a perspective view showing a game space of the forming position of the radiant film; and FIG. 8 are a plan view and side views of a space where the forming position of the radiant film includes a plurality of seats.

MODE FOR CARRYING OUT THE INVENTION

An infection prevention device according to a first embodiment of the present invention includes a light source for radiating light in a specific wavelength rang, and a beam-firming optical element for forming light radiated from the light source on a radiant film having a specific width, in which pathogenic microorganism which levitates together with airborne droplets or particles by the radiant film formed in air or pathogenic microorganism which alone levitate in air is inactivated or killed, or moisture of the airborne droplets or particles is evaporated. According to this embodiment, levitating pathogenic microorganism is inactivated or killed, or airborne droplets or particles are evaporated, thereby effectively preventing infection especially in an overcrowding, cohesive and closed room.

According to a second embodiment of the invention, in the infection prevention device of the first embodiment, the infection prevention device described in the first embodiment further includes a damper placed on a terminal end of the radiant film, wherein the damper is made of low reflection material. In this embodiment, it is possible to prevent light forming the radiant film from reflecting or scattering at a terminal end.

According to a third embodiment of the invention, in the infection prevention device of the first or second embodiment, the radiant film is formed in a doorway of a room or a zone in this embodiment, it is possible to prevent the pathogenic microorganism from a doorway from moving.

According to a fourth embodiment of the invention, in the infection prevention device of the first or second embodiment, the radiant film is formed between opposed persons. In this embodiment, it is possible to prevent infection caused by pathogenic microorganism which levitates especially together with airborne droplets.

According to a fifth embodiment of the invention, in the infection prevention device of the first or second embodiment, the radiant film is formed between a stage and an audience seat. In this embodiment, it is possible to prevent pathogenic microorganism from moving between the stage and the audience seats.

According to a sixth embodiment of the invention, in the infection prevention device of the first or second embodiment, the radiant film is formed into the cylindrical shape, and a space is formed in the radiant film which is formed into a cylindrical shape. In this embodiment, it is possible to prevent pathogenic microorganism from flowing out from a space formed in the radiant film or to prevent the pathogenic microorganism from flowing into the space formed in the radiant film.

According to a seventh embodiment of the invention, in the infection prevention device of the first or second embodiment, the radiant film is formed on an outer periphery of a game space. In this embodiment, it is possible to isolate the game space, and to prevent the pathogenic microorganism from flowing into the game space or to prevent the pathogenic microorganism from flowing out from the game space.

According to an eighth embodiment of the invention, in the infection prevention device of the first or second embodiment, the infection prevention device described in the first or second embodiment further comprises at least one more radiant film, wherein the radiant film or the radiant films are formed on a side or in front of or behind a seat. In this embodiment, it is possible to prevent the pathogenic microorganism from moving between the seats, and to prevent infection between the cohesive seats.

According to a ninth embodiment of the invention, in the infection prevention device of any one of the first to eighth embodiments, the light source and the beam-firming optical element are placed at high positions, and the radiant film is formed by radiating the light from upward to downward. In this embodiment, it is difficult to visually see as compared with the direction from downward to upward, and as compared with formation of the radiant film in the lateral direction. Therefore, it is possible to mitigate influence on human eyes.

According to a tenth embodiment of the invention, in the infection prevention device of any one of the first to ninth embodiments, the light source is composed of a coherent light source, an ultraviolet ray laser or laser, and a wavelength converting device. In this embodiment, it is easy to form a radiant film having a specified wavelength range.

According to an eleventh embodiment of the invention, in the infection prevention device of any one of the first to tenth embodiments, as the beam-firming optical element, at least any one of a beam expander which widens the light, a cylindrical lens which makes the light laterally long, and a condenser lens which makes the light as parallel light is used. In this embodiment, by using the beam expander, the cylindrical lens, and the condenser lens, it is possible to form a radiant film having a predetermined thickness and a predetermined width.

According to a twelfth embodiment of the invention, in the infection prevention device of the second embodiment, as the damper, black almite is used. In this embodiment, it is possible to prevent light forming the radiant film from reflecting or scattering at the terminal end.

According to an infection prevention device of a thirteenth embodiment of the invention, a lamp, a light-emitting diode or a semiconductor laser is used as a light source which radiates light in specific wavelength range, and pathogenic microorganism which levitates together with airborne droplets or particles or which levitates along is inactivated or killed by forming, in air, a radiant film having a predetermined width by the light radiated from the light source. In this embodiment, levitating pathogenic microorganism is inactivated or killed, or airborne droplets or particles are evaporated, thereby effectively preventing infection especially in an overcrowding, cohesive and closed room.

According to a fourteenth of the invention, in the infection prevention device of any one of the first to thirteenth embodiments, the specific wavelength range is wavelength range in a range of 190 nm to 350 nm, and the radiant film is formed by average output of 20 W or less per 1 m width. In this embodiment, it is possible to obtain a radiant film having small influence on a human body.

According to a fifteenth embodiment of the invention, in the infection prevention device of any one of the first to thirteenth embodiments, the specific wavelength range is infrared radiation range of 800 nm or more. In this embodiment, by evaporating moisture of the airborne droplets or the particles, it is possible to prevent airborne droplet infection, and a possibility that the pathogenic microorganism is inactivated or killed by heat generated when moisture is evaporated is increased.

According to a sixteenth embodiment of the invention, in the infection prevention device of any one of the first to ninth embodiments, an ultrashort pulse laser is used as the light source, and the specific wavelength range is a visual radiation region or an infrared radiation range of 400 nm or more. In this embodiment, harm inflicted on human body such as ultraviolet radiation is small, and inactivation of pathogenic microorganism can be carried out by energy of photon in an ultraviolet 0.3 radiation range.

According to a seventeenth embodiment of the invention, in the infection prevention device of any one of the first to sixteenth embodiments, the radiant film is turned back around a reflection plate, thereby forming at least two radiant films. In this embodiment, the number of the radiant films is two or more. According to this, pathogenic microorganism which levitates together with airborne droplets or particles or pathogenic microorganism which levitates alone is not inactivated or killed in the first radiant film, or even when moisture of the airborne droplets or particles are not sufficiently evaporated, the pathogenic microorganism is inactivated or killed in the second radiant film and moisture of the airborne droplets or particles can sufficiently be evaporated.

According to an eighteenth embodiment of the invention, in the infection prevention device of the seventeenth embodiment, the first radiant film and the second radiant film are not parallel to each other. In this embodiment, as compared with a case where the first radiant film and the second radiant film are formed in parallel to each other, a higher barrier effect can be expected.

According to a nineteenth embodiment of the invention, the infection prevention device of any one of the first to sixteenth embodiments further includes at least one more light source, thereby forming at least two radiant films. In this embodiment, the number of the radiant films is two or more. According to this, pathogenic microorganism which levitates together with airborne droplets or particles or pathogenic microorganism which levitates alone is not inactivated or killed in the first radiant film, or even when moisture of the airborne droplets or particles are not sufficiently evaporated, the pathogenic microorganism is inactivated or killed in the second radiant film and moisture of the airborne droplets or particles can sufficiently be evaporated.

According to a twentieth embodiment of the invention, in the infection prevention device of the nineteenth embodiment, center wavelengths of the light sources are different from each other. In this embodiment, the plurality of radiant films have different center wavelengths. According to this, it is possible to combine wavelength range having a high inactivating or killing effect and wavelength range having a high moisture evaporation effect, and a high barrier effect can be expected.

According to a twenty-first embodiment of the invention, the infection prevention device of any one of the first to twentieth embodiments, further including a detector 15 which detects scattering light from the radiant film, wherein if the detector detects the scattering light of a predetermined value or more, radiation of the light from the light source is stopped. In this embodiment, even if a radiant film has wavelength range which is not preferable for human body, if scattering light is generated depending upon using news conference or using status, irradiation of the light can be stopped. Therefore, safety can be secured.

According to a twenty-second embodiment of the invention, in the infection prevention device of the twenty-first embodiment, the detector is placed on the side of the light source, and a detection direction of the detector is a radiation direction of the light. In this embodiment, it is possible to effectively detect scattering light from the radiant film.

According to a twenty-third embodiment of the invention, in the infection prevention device of the first or thirteenth embodiment, interference light in a wavelength range which is different from the specific wavelength range of the light which forms the radiant film is radiated to the radiant film, and a position where the interference light is radiated is at a terminal end of the radiant film. In this embodiment, it is possible to prevent light forming the radiant film from reflecting or scattering at the terminal end without providing a physical damper.

According to an infection prevention method of a twenty-fourth embodiment of the invention, a radiant film having a predetermined width is formed by light in a specific wavelength range, pathogenic microorganism which levitates together with airborne droplets or particles or which levitates alone is inactivated or killed, or moisture of the airborne droplets or the particles is evaporated. In this embodiment, by inactivating or killing, in air, the levitating pathogenic microorganism, or by evaporating moisture of the airborne droplets or particles, it is possible to effectively prevent infection in an overcrowding, cohesive and closed room.

Embodiment

An embodiment of the present invention will be described below together with drawings.

FIG. 1 are diagrams showing a configuration of an infection prevention device of the embodiment.

As shown in FIG. 1(*a*), the infection prevention device 10 of the embodiment includes a light source 11 for radiating light in a specific wavelength range, a beam-firming optical element 12 for forming light radiated from the light source 11 on a radiant film 20 having a predetermined width, and a damper 13 located at a terminal end of the radiant film 20.

As the light source 11, a coherent light source, an ultraviolet ray laser, or a light source composed of a laser and a wavelength converting device is used. By using such a light source 11, it is easy to form the radiant film 20 having a specified wavelength range.

An ultrashort pulse laser can be used as the light source 11. If the ultrashort pulse laser is used as the light source 11, it is possible to obtain light having high electric field intensity from its property. It is found that the light having high electric field intensity acts such that a plurality of photons acts as one photon which is called non-linear process or multiphoton process. Energy of photon of 260 nm is equal to three photons of 780 nm. Therefore, an ultrashort pulse laser of wavelength of 780 nm can give molecule the same absorption characteristics as 260 nm in three photons. That is, inactivation of pathogenic microorganism using wavelength of ultraviolet region can be obtained by an ultrashort pulse laser of two times, three times or four times wavelength of ultraviolet region.

Therefore, if an ultrashort pulse laser in visual radiation range or infrared radiation range of 400 nm or more is used, it is possible to carry out inactivation of pathogenic microorganism with small harm on human body such as ultraviolet radiation. As the ultrashort pulse laser by the infrared radiation in a range of 800 nm to 1 mm, wavelength of 800 nm, 1030 nm or 1500 nm is suitable.

As a specific wavelength range, it is possible to use wavelength range of 190 nm to 350 nm. For example, when wavelength range of 225 nm is used, sterilization force of 2 mW/cm$^2$ for one second is 95% or more. If speed of airborne droplets is in a range of 30 cm/second to 80 cm/second, time during which the airborne droplets pass for 1 mm is 3.3×10 seconds to 1.25×10$^{-3}$ seconds. Therefore, when a film thickness of the radiant film 20 is 1 mm and a width of the radiant film 20 is 1 m, average output is 6 W to 16 W and sufficient sterilization force can be obtained.

As described above, the specific wavelength range is set to wavelength range in a range of 190 nm to 350 nm, the radiant film 20 is formed with average output of 20 W or less per 1 m width. According to this, it is possible to obtain the radiant film 20 having small influence on human body. When the wavelength range in a range of 190 nm to 350 nm is used, it is effective that the center wavelength is 215 nm or 266 nm. Especially when the center wavelength is set to 215 nm, acute disorder of skin is not generated and safety is high.

As the specific wavelength range, ultraviolet radiation of 350 nm to 400 nm, and infrared radiation of 800 nm to 1 mm, especially 1.5 μm to 2.0 μm can also be used. When the infrared radiation is used, airborne droplet infection can be prevented by evaporating moisture of airborne droplets or particles, and inactivating or killing effect of pathogenic microorganism caused by heat when moisture is evaporated can be expected.

As the beam-firming optical element 12, at least any of a beam expander which widens light, a cylindrical lens which makes light laterally long, and a condenser lens which makes light as parallel light is used. If the beam expander, the cylindrical lens and the condenser lens are used in combination in this manner, it is possible to form the radiant film 20 having a predetermined thickness and a predetermined width.

Low reflection material can be used as the damper 13, and black almite can be used as the low reflection material. If the damper 13 is used in this manner, it is possible to prevent light forming the radiant film 20 from reflecting or scattering at the terminal end.

The infection prevention device 10 of the embodiment inactivates or kills pathogenic microorganism which levitates together with airborne droplets or particles or which levitates along by the radiant film 20 which is formed in air.

The pathogenic microorganism is classified into bacterium, rickettsia, virus or the like, and fungus, protozoal, infestant and venomous creature also exist as the pathogenic microorganism.

By inactivating or killing the levitating pathogenic microorganism in air, it is possible to effectively prevent infection in the overcrowding, cohesive and closed room.

FIG. 1(*b*) shows a case where the infection prevention device of the embodiment is used as a vertical type device, and FIG. 1(*c*) shows a case where the infection prevention device of the embodiment is used as a lateral type device.

Arrows in the drawings show radiation direction of light forming the radiant film 20.

As shown in FIG. 1(*b*), when the light source 11 and the beam-firming optical element 12 are placed at higher locations and the radiant film 20 is formed by radiating light from upward to downward, it is difficult to visually see as compared with a case from downward to upward, and as compared with a case where the radiant film 20 is formed in the lateral direction. Therefore, influence on human eyes can be reduced.

FIG. 1(*c*) shows a case where a plane of the radiant film 20 is a vertical plane, but the plane of the radiant film 20 may be a horizontal plane, or the plane of the radiant film 20 may be inclined from the horizontal plane by a predetermined angle.

As shown in FIG. 1, the radiant film 20 is formed by light radiated from the light source 11, the radiant film 20 is formed without using reflection light, but at least a portion of reflection light may be superposed on a forming position of the radiant film 20, and a reflection member may be placed instead of the damper 13. When the reflection member is placed instead of the damper 13, it is preferable that the radiant film 20 is formed without scattering the reflection light by the reflection member.

Although the low reflection material is used as the damper 13 in this embodiment, it is also possible to use, as the damper 13, light-absorptive material, wavelength changing material or a structure member which does not discharge incident light.

FIGS. 1(*d*) and 1(*e*) are sectional views taken along an X-X line shown in FIGS. 1(*b*) and 1(*c*), and FIGS. 1(*d*) and 1(*e*) show cross sectional shapes of the radiant film 20, As show in FIGS. 1(*d*) and 1(*e*), the radiant film 20 is formed by radiation light of one direction, and at least a size of the radiant film 20 in its width direction is made longer than a thickness of the radiant film 20. In this embodiment, the radiation light of one direction forming the radiant film 20 is a parallel light.

FIG. 2 are diagrams sowing configuration of an infection prevention device according to another embodiment of the invention. FIG. 2(*a*) is a conceptual side view of the infection prevention device, and FIGS. 2(*b*) and 2(*c*) are conceptual sectional views taken along a Y-Y line shown in FIG. 2(*a*).

As shown in FIG. 2(*a*), according to the infection prevention device 10 of the embodiment, a lamp, a light-emitting diode or a semiconductor laser is used as light sources 14 which radiates light of specific wavelength range, a radiant film 20 having a predetermined width by light radiated from the light sources 14 is formed in air, thereby inactivating or killing pathogenic microorganism which levitates together with airborne droplets or particles or which levitates alone.

In FIG. 2(*a*), four light sources 14*a*, 14*b*, 14*c* and 14*d* are provided as the light sources 14.

The light source 14*a* forms a radiant film 20*a*, the light source 14*b* forms a radiant film 20*b*, the light source 14*c* forms a radiant film 20*c* and the light source 14*d* forms a radiant film 20*d*.

The radiant films 20*a*, 20*b*, 20*c* and 20*d* may be radiant films 20 which enlarge into a conical shape as shown in FIG. 2(*b*), or may be radiant films 20 which enlarge into a rectangular shape as shown in FIG. 2(*c*). In the case of the radiant films 20 which enlarge into the conical shape shown in FIG. 2(*b*), or in the case of the radiant films 20 which enlarge into the rectangular shape, sizes in the thickness direction are constant thickness, and only sizes in their width direction are enlarged.

The radiant films 20*a*, 20*b*, 20*c* and 20*d* of the embodiment are formed by radiation light of one direction, and at least sizes in their width direction are made longer than thicknesses of the radiant films 20. In this embodiment, radiation light of one direction forming the radiant film 20 is not parallel light but is light which enlarges radially.

In this embodiment, the light sources 14*a*, 14*b*, 14*c* and 14*d* are placed such that at least portions of the plurality of radiant films 20*a*, 20*b*, 20*c* and 20*d* are superposed on each other in a width direction of the radiant film 20. By placing the plurality of light sources 14*a*, 14*b*, 14*c* and 14*d* and the plurality of radiant films 20*a*, 20*b*, 20*c* and 20*d* are superposed on each other in the width direction of the radiant film 20 in this manner, a high barrier effect can be expected. Especially, the radiant films 20 which are not parallel light but are enlarged radially are superposed on each other in the width direction. According to this, light can be radiated from different direction to pathogenic microorganism which levitates together with airborne droplets or particles or which levitates alone. Therefore, a higher barrier effect can be expected.

Since the infection prevention device 10 of this embodiment has a high barrier effect at a center portion thereof as compared with a periphery thereof, it is effective to use the infection prevention device 10 between a stage 61 (see FIG. 6) and audience seats 62 (see FIG. 6).

The infection prevention device 10 of this embodiment includes detectors 15 which detect scattering light from the radiant film 20. Each of the detectors 15 is placed on the side of the light source 14, and a detecting direction of the detector 15 is a radiation direction of light from the light source 14. BY setting the detection direction of the detector 15 as the radiation direction of light, it is possible to effectively detect scattering light from the radiant film 20.

The detector 15*a* detects scattering light of the radiant film 20*a* mainly by the light source 14*a*, the detector 15*b* detects scattering light of the radiant film 20*b* mainly by the light source 14*b*, the detector 15*c* detects scattering light of the radiant film 20*c* mainly by the light source 14*c*, and the detector 15*d* detects scattering light of the radiant film 20*d* mainly by the light source 14*d*.

If the detector 15 detects scattering light of a predetermined value or more, radiation from the light source 14 is stopped. Therefore, even if a radiant film 20 has wavelength range which is not preferable for human body, if scattering light is generated depending upon using environment or using status, radiation of light can be stopped. Therefore, safety can be secured.

In this embodiment, since the plurality of light sources 14 are provided, if the detector 15*a* detects scattering light of a predetermined value of more, radiation of light from the light source 14*a* is stopped, if the detector 15*b* detects scattering light of a predetermined value of more, radiation of light from the light source 14*b* is stopped, if the detector 15*c* detects scattering light of a predetermined value of more, radiation of light from the light source 14*c* is stopped, and if the detector 15*d* detects scattering light of a predetermined value of more, radiation of light from the light source 14*d* is stopped.

Since the respective light sources 14 stop the radiation of light in this manner, it is possible to secure safety by scattering light, and it is possible to maintain barrier function by the light source 14 where scattering light is not generated.

By such radiant films 20 also, it is possible to inactivate or kill levitating pathogenic microorganism in air, and it is possible to effectively prevent infection in an overcrowding, cohesive and closed room.

In the case of the radiant films 20 which enlarge radially as in this embodiment, it is especially effective to provide the damper 13.

In this embodiment also, the radiant film 20 is formed by light radiated from the light source 14, and the radiant film 20 is formed without using reflection light, but at least a portion of reflection light may be superposed on the forming position of the radiant film 20, and a reflection member may be placed instead of the damper 13.

As the damper 13, in addition to the low reflect lion material, it is also possible to use light-absorptive material, wavelength changing material or a structure member which does not discharge incident light.

FIGS. 3 to 7 are conceptual diagrams showing the forming position of the radiant film by the infection prevention device shown in FIG. 1 or 2. Description of the damper 13 and the other configuration will be omitted.

FIG. 3(*a*) is a plan view of rooms or zones which is partitioned by a predetermined partition, and FIGS. 3(*b*) and 3(*c*) are side views taken along a Z-Z line in FIG. 3(*a*).

In FIG. 3(*a*), the radiant film 20 is formed in a doorway 33 between one of the rooms (zone) 31 and the other room (zone) 32 which is adjacent to the room (zone) 31, and another radiant film 20 is formed in a doorway 34 of the room 32.

As shown in FIG. 3(*b*), the infection prevention device 10 is formed at a high position, and light is radiated from upward to downward, thereby forming the radiant films 20.

The infection prevention device 10 of this embodiment includes the detector 15 which detects scattering light from the radiant film 20. The detector 15 is placed on the side of the light source 11, and a detection direction of the detector 15 is a radiation direction of light from the light source 11. By setting the detection direction of the detector 15 as the radiation direction of light, it is possible to effectively detect scattering light from the radiant film 20.

If the detector 15 detects scattering light of a predetermined value or more, radiation of light from the light source 11 is stopped. Therefore, even if a radiant film 20 has wavelength range which is not preferable for human body, if scattering light is generated depending upon using environment or using status, radiation of light can be stopped. Therefore, safety can be secured.

The damper 13 is placed at the terminal end of the radiant film 20, i.e., below the infection prevention device 10.

By placing the damper 13, it is possible to prevent light forming the radiant film 20 from reflecting or scattering at the terminal end. As the damper 13, in addition to the low reflection material, it is also possible to use light-absorptive material, wavelength changing material or a structure member which does not discharge incident light.

Further, as shown in FIG. 3(*c*), by placing a reflection plate 16 below the infection prevention device 10 and by turning back the radiant film 20 around the reflection plate 16, it is possible to form at least two radiant films 20*x* and 20*y*.

Two or more radiant films 20 are provided in this manner, even if pathogenic microorganism which levitates together with airborne droplets or particles or which levitates alone is not inactivated or killed, or even if moisture or airborne droplets or particles is not sufficiently evaporated by the first radiant film 20*x*, the pathogenic microorganism can be inactivated or killed or moisture of the airborne droplets or the particles can be evaporated by the second radiant film 20*y*.

When two or more radiant films 20 are provided in this manner, it is preferable that the first radiant film 20*x* and the second radiant film 20*y* are not parallel to each other. If the first radiant film 20*x* and the second radiant film 20*y* are not parallel to each other, high barrier effect can be expected as compared with a case where the first radiant film 20*x* and the second radiant film 207 are parallel to each other.

According to this embodiment, it is possible to prevent pathogenic microorganism from moving from the doorways 33 and 34.

More precisely, it is effective to form the radiant film 20 in the doorway of a patient room, a doorway of hospital ward, a doorway of a stairs, an elevator and an entrance, or a doorway of a food factory or a plant factory.

It is also effective to form the radiant film 20 not only in the doorways 33 and 34, but also in a boundary between infection zone and non-infection zone.

If the radiant film 20 is formed along a line on the line or on the side of the line of the food factory, it is possible to sterilize food on the line.

FIG. 4 is a side view of a predetermined space such as a room.

In FIG. 4, in the predetermined space 40, the radiant film 20 is formed between opposed persons 41 and 42.

More specifically, the predetermined space 40 can be used in a news conference room, a teaching room, a conference room or a dining room. The radiant film 20 is formed between an interview person and a reporter in the news conference room, and between a teacher and a student in the teaching room.

As shown in FIG. 4, the infection prevention device 10 is placed at a high position, and the radiant film 20 is formed by radiating light from upward to downward.

The infection prevention device 10 of the embodiment includes the detector 15 which detects scattering light from the radiant film 20. The detector 15 is placed on the side of the light source 11, and a detection direction of the detector 15 is a radiation direction of light from the light source 11. By setting the detection direction of the detector 15 as the radiation direction of light, it is possible to effectively detect scattering light from the radiant film 20.

If the detector 15 detects scattering light of a predetermined value or more, radiation of light from the light source 11 is stopped. Therefore, even if a radiant film 20 has wavelength range which is not preferable for human body, if scattering light is generated depending upon using environment or using status, radiation of light can be stopped. Therefore, safety can be secured.

The damper 13 is placed at the terminal end of the radiant film 20, i.e., below the infection prevention device 10.

By placing the damper 13, it is possible to prevent light forming the radiant film 20 from reflecting or scattering at the terminal end. As the damper 13, in addition to the low reflection material, it is also possible to use light-absorptive material, wavelength changing material or a structure member which does not discharge incident light.

According to the infection prevention device 10 of this embodiment, at least two radiant films 20e and 20f are formed by providing a plurality of light sources 11e and 11f. By providing two or more radiant films 20 in this manner, even if pathogenic microorganism which levitates together with airborne droplets or particles or which levitates alone is not inactivated or killed, or even if moisture of airborne droplets or particles is not sufficiently evaporated by the first radiant film 20e, the pathogenic microorganism can be inactivated or killed or moisture of the airborne droplets or the particles can be evaporated by the second radiant film 20f.

When the plurality of radiant films 20 are formed in this manner, it is also effective that center wavelengths of the light sources 11e and 11r are different. If the plurality of radiant films 20e and 20f having different center wavelengths, it is possible to combine a wavelength range where the inactivating or killing effect is high and a wavelength range where moisture evaporating effect is high, and high barrier effect can be expected.

According to this embodiment, it is especially possible to prevent infection caused by pathogenic microorganism which levitates together with airborne droplets.

FIG. 5 is a perspective view of a predetermined space such as a conference room.

In FIG. 5, in the conference room 50, the radiant film 20 is formed between opposed persons 41 and 42 and at a position higher than a table 51.

Although the light source 11 forming the radiant film 20 is placed at a high position in FIG. 5, the light source 11 may be placed on the table 51 and light may be radiated from downward to upward.

As shown in FIG. 5, when the radiant film 20 is used on the table 51, it is preferable to provide the detectors 15 which detect scattering light from the radiant film 20.

If the detectors 15 detect scattering light of a predetermined value or more, radiation of light from the light source 11 is stopped. Therefore, even if a radiant film 20 has wavelength range which is not preferable for human body, if scattering light of the predetermined value or more is detected depending upon using environment, it becomes impossible to use the infection prevention device 10 of this embodiment, and when scattering light of the predetermined value or more is not detected depending upon the using environment, it becomes possible to use the infection prevention device 10 of the embodiment.

Further, even if the infection prevention device 10 can be used depending upon the using environment, if scattering light is generated depending upon the using status, since radiation of light can be stopped, safety can be secured even while the infection prevention device 10 is used.

Although the conference room 50 is shown in FIG. 5, it is also effective to form the radiant film 20 between the opposed persons 41 and 42 like a drinking spot, a restaurant, a cafe and the like.

According to this embodiment, it is especially possible to prevent infection caused by pathogenic microorganism which levitates together with airborne droplets.

FIG. 6 is a side view showing a portion of a hall having a stage and audience seats.

As shown in FIG. 6, by forming the radiant films 20 between the stage 61 and the audience seats 62, it is possible to prevent pathogenic microorganism from moving between the stage 61 and the audience seats 62.

FIG. 6 shows a case where a radiant film 20A and a radiant film 20B are provided between the stage 61 and the audience seats 62. The radiant film 20A is the infection prevention device 10 shown in FIG. 1, and the radiant film 20B is the infection prevention device 10 shown in FIG. 2.

In FIG. 6, the radiant film 20 (20C) is formed into a cylindrical shape, and a space is formed in the cylindrical radiant film 20C.

According to the radiant film 20C, it is possible to prevent pathogenic microorganism from flowing out from a space formed in the radiant film 20C, or to prevent pathogenic microorganism from flowing into the space formed in the radiant film 20C.

FIG. 7 is a perspective view showing a game space.

As shown in FIG. 7, by forming the radiant films 20 on an outer periphery of the game space 70, it is possible co separate the game space 70 from the audience seats 71, and it is possible co prevent pathogenic microorganism from flowing into or flowing out from the game space 70.

When a plurality of game spaces 70 are adjacently provided for example, if the radiant films 20 are formed for the respective game spaces 70, it is possible to prevent pathogenic microorganism from flowing into and flowing out from the game spaces 70.

FIG. 8(a) is a plan view showing a space having a plurality of seats.

As shown in FIG. 8(a), the radiant films 20 are formed on the side of or in front of or behind the seats 80. According to this, it is possible to prevent pathogenic microorganism from moving between the seats 80, and to prevent infection between cohesive seats 80.

It is preferable to place the light source 11 forming the radiant film 20 on a floor surface. It is preferable that the light sources 11 located on the side of or in front of or behind the seats 80 are supplied from an optical fiber 17

FIG. 8(b) is a conceptual side view of a portion of FIG. 8(a).

In FIG. 8(b), interference light 18 in wavelength range which is different from specific wavelength range of light forming the radiant film 20 is radiated to the radiant film 20, and a position W where the interference light 18 is radiated is a terminal end of the radiant film 20. The interference light 18 is formed in a film-shape by a light source 19 and is radiated.

In this manner, by radiating, to the radiant film 20, the interference light 18 in the wavelength range which is different from the specific wavelength range of light forming the radiant film 20 to change the wavelength of the radiant film 20, even if a radiant film 20 has the wavelength range which is not preferable for human body, it is possible to prevent light forming the radiant film 20 from reflecting or scattering at the terminal end without providing a physical damper 13.

More specifically, the radiant film 20 can be formed between the seats 80 in a movie theater, a concert hall and a vehicle such as a Shinkansen bullet train.

As described above, the radiant film 20 having a predetermined width is formed by light in the specific wavelength range, and pathogenic microorganism which levitates together with airborne droplets or a particles or which levitates alone is inactivated or killed by the radiant film 20 which is formed in air. According to this, it is possible to effectively prevent infection in an overcrowding, cohesive and closed room.

INDUSTRIAL APPLICABILITY

According to the present invention, the infection prevention device can be placed in a predetermined space and used, but the infection prevention device can also be attached to a millinery and a hat and used.

EXPLANATION OF SYMBOLS 10 infection prevention device
11, 11e, 11f light source
12 beam-firming optical element
13 damper
14, 14a, 14b, 14c, 14d light source
15, 15a, 15b, 15c, 15d detector
16 reflection plate
17 optical fiber
18 interference light
19 interference light source
20, 20a, 20b, 20c, 20d, 20e, 20f, 20x, 20y, 20A, 20B, 20C radiant film
31, 32 room (zone)
33, 34 doorway
40 predetermined space
41, 42 person
50 conference room
51 table
61 stage
62, 71 audience seat
70 game space
80 seat
W position

The invention claimed is:

1. An infection prevention device comprising
a light source for radiating light in specific wavelength range, and
a beam-firming optical element for forming the light radiated from the light source on a radiant film having an adjustable width, wherein
pathogenic microorganism which levitates together with airborne droplets or particles or which levitates alone is inactivated or killed by the radiant film formed in air, or moisture of the airborne droplets or the particles is evaporated.

2. The infection prevention device according to claim 1, further comprising a damper placed on a terminal end of the radiant film, wherein
the damper is made of low reflection material.

3. The infection prevention device according to claim 2, wherein as the damper, black almite is used.

4. The infection prevention device according to claim 1, wherein the radiant film is formed in a doorway of a room or a zone.

5. The infection prevention device according to claim 1, wherein the radiant film is formed between opposed persons.

6. The infection prevention device according to claim 1, wherein the radiant film is formed between a stage and an audience seat.

7. The infection prevention device according to claim 1, wherein the radiant film is formed into the cylindrical shape, and
a space is formed in the radiant film which is formed into a cylindrical shape.

8. The infection prevention device according to claim 1, wherein the radiant film is formed on an outer periphery of a game space.

9. The infection prevention device according to claim 1, further comprising at least one more radiant film, wherein the radiant film or the radiant films are formed on a side or in front of or behind a seat.

10. The infection prevention device according to claim 1, wherein the light source and the beam-firming optical element are placed at high positions, and
the radiant film is formed by radiating the light from upward to downward.

11. The infection prevention device according to claim 1, wherein the light source is composed of a coherent light source, an ultraviolet ray laser or laser, and a wavelength converting device.

12. The infection prevention device according to claim 1, wherein as the beam-firming optical element, at least any one of a beam expander which widens the light, a cylindrical lens which makes the light laterally long, and a condenser lens which makes the light as parallel light is used.

13. The infection prevention device according to claim 1, wherein the specific wavelength range is wavelength range in a range of 190 nm to 350 nm, and the radiant film is formed by average output of 20 W or less per 1 m width.

14. The infection prevention device according to claim 1, wherein the specific wavelength range is infrared radiation range of 800 nm or more.

15. The infection prevention device according to claim 1, wherein an ultrashort pulse laser is used as the light source, and the specific wavelength range is visual radiation region or infrared radiation range of 400 nm or more.

16. The infection prevention device according to claim 1, wherein the radiant film is turned back around a reflection plate, thereby forming at least two radiant films.

17. The infection prevention device according to claim 16, wherein the first radiant film and the second radiant film are not parallel to each other.

18. The infection prevention device according to claim 1, further comprising at least one more light source, thereby forming at least two radiant films.

19. The infection prevention device according to claim 18, wherein center wavelengths of the light sources are different from each other.

20. The infection prevention device according to claim 1, further comprising a detector which detects scattering light from the radiant film, wherein if the detector detects the scattering light of an adjustable value or more, radiation of the light from the light source is stopped.

21. The infection prevention device according to claim 20, wherein the detector is placed on the side of the light source, and a detection direction of the detector is a radiation direction of the light.

22. The infection prevention device according to claim 1, wherein interference light in a wavelength range which is different from the specific wavelength range of the light which forms the radiant film is radiated to the radiant film, and a position where the interference light is radiated at a terminal end of the radiant film.

23. An infection prevention device wherein
a lamp, a light-emitting diode or a semiconductor laser is used as a light source which radiates light in specific wavelength range, and
pathogenic microorganism which levitates together with airborne droplets or particles or which levitates alone is inactivated or killed by forming, in air, a radiant film having an adjustable width by the light radiated from the light source.

24. An infection prevention method wherein a radiant film having an adjustable width is formed by light in a specific wavelength range, pathogenic microorganism which levitates together with airborne droplets or particles or which levitates alone is inactivated or killed, or moisture of the airborne droplets or the particles is evaporated.

\* \* \* \* \*